United States Patent [19]

Bourdauducq et al.

[11] 4,243,606
[45] Jan. 6, 1981

[54] N-SUBSTITUTED ANILINES

[75] Inventors: Paul M. C. Bourdauducq, Franqueville St Pierre; Claude M. H. E. Brouard, St Pierre les Elbeuf; Claude L. E. Moerel, Bihorel; Jean-Pierre H. Stiot, St Pierre les Elbeuf, all of France

[73] Assignee: Produits Chimiques Ugine Kuhlmann, Courbevoie, France

[21] Appl. No.: 838,438

[22] Filed: Sep. 30, 1977

[30] Foreign Application Priority Data

Oct. 12, 1976 [FR] France .............................. 76 30578

[51] Int. Cl.³ ................ C07C 101/447; C07C 103/28; C07C 121/78
[52] U.S. Cl. .............................. 260/465 D; 260/205; 260/206; 260/207; 260/207.1; 260/207.5; 260/465 E; 260/465 G; 560/19; 560/43; 560/44; 560/45; 560/47; 560/250; 560/251; 562/433; 562/452; 562/456; 564/163
[58] Field of Search .......... 260/465 E, 465 D, 558 A, 260/559 A; 560/19, 43, 44, 45, 47, 250; 562/433, 452, 456

[56] References Cited

U.S. PATENT DOCUMENTS

| 2,592,364 | 4/1952 | Weissberger et al. | 260/465 E X |
| 3,522,234 | 7/1970 | Groebke et al. | 260/465 D X |
| 3,892,725 | 7/1975 | Stiot et al. | 260/157 |

FOREIGN PATENT DOCUMENTS 1199751 12/1959 France .
1205351 2/1960 France .

Primary Examiner—Dolph H. Torrence
Attorney, Agent, or Firm—Beveridge, DeGrandi, Kline & Lunsford

[57] ABSTRACT

The present invention relates to new N-substituted anilines which correspond to the general formula:

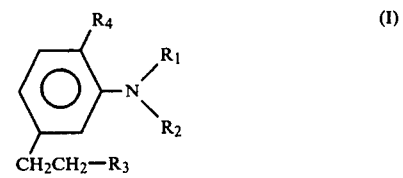

in which $R_1$ represents an alkyl radical or substituted alkyl radical, $R_2$ represents a hydrogen atom, an alkyl radical or substituted alkyl radical, $R_3$ represents a cyano, carbamoyl, carboxy or carbalkoxy radical and $R_4$ represents a hydrogen or halogen atom or an alkyl or alkoxy radical. These compounds are valuable intermediates for the preparation of coloring materials, especially as coupling compounds for the synthesis of azo dyes.

10 Claims, No Drawings

N-SUBSTITUTED ANILINES

BACKGROUND OF THE INVENTION

Field of the Invention

The present invention relates to new N-substituted anilines, utilizable especially for the preparation of coloring materials.

SUMMARY OF THE INVENTION

The new compounds according to the invention correspond to the general formula:

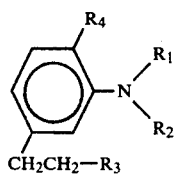

in which $R_1$ represents an alkyl radical or substituted alkyl radical, $R_2$ represents a hydrogen atom, an alkyl radical or substituted alkyl radical, $R_3$ represents a cyano, carbamoyl, carboxy or carbalkoxy radical, and $R_4$ represents a hydrogen or halogen atom or an alkyl or alkoxy radical.

DESCRIPTION OF THE PREFERRED EMBODIMENTS

The alkyl or alkoxy radicals may contain 1 to 4 carbon atoms and are preferably those containing 1 or 2 carbon atoms. When $R_3$ represents a carbalkoxy radical, this may contain 2 to 5 carbon atoms and is preferably the carbomethoxy or carbethoxy radical. Possible substituents of the alkyl radicals $R_1$ and $R_2$ are the halogen atoms (for example, chlorine or bromine), but especially the hydroxy, cyano, alkoxy (for example, methoxy or ethoxy), acyloxy (for example, acetoxy or propionyloxy) and carbalkoxy (for example, carbomethoxy or carbethoxy) groups. When $R_4$ is halogen, this is preferably chlorine or bromine.

The compounds of formula (I) may be prepared by methods known per se (Meerwein reaction, reduction, alkylation, hydrolysis, acylation, esterification) from m-nitranilines of the formula:

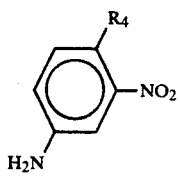

in which $R_4$ has the same significance as above.

There is obtained according to the reaction of Meerwein by the action of acrylonitrile or an alkyl acrylate on a diazonium halide of an m-nitraniline of formula (II) in the presence of a copper salt as catalyst, a compound of the formula:

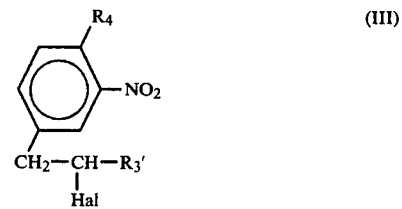

in which "Hal" denotes a halogen atom, preferably chlorine, and $R'_3$ represents a cyano or carbalkoxy radical containing 2 to 5 carbon atoms (preferably carbomethoxy or carbethoxy).

By reduction of the compounds of formula (III), anilines of the following formula are then obtained:

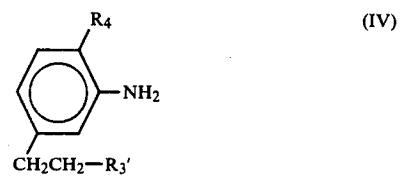

in which $R'_3$ and $R_4$ have the same significance as above.

On treatment of the anilines of formula (IV) with an alkylating agent such as, for example, methyl or ethyl bromide, dimethyl or diethyl sulphate, glycol chlorhydrin, β-chlorethyl p-toluenesulphonate, methyl or ethyl acrylate, or acrylonitrile, compounds are obtained according to the invention of the formula:

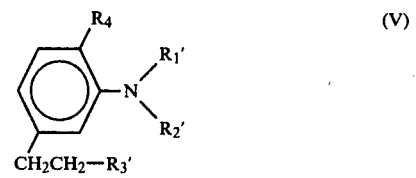

in which $R'_3$ and $R_4$ have the same significance as above, $R'_1$ represents an alkyl, hydroxyalkyl, haloalkyl, carbalkoxyalkyl or cyanalkyl radical and $R'_2$ represents a hydrogen atom or an alkyl, hydroxyalkyl, haloalkyl, carbalkoxyalkyl or cyanalkyl radical. The monoalkylation leads to the compounds of formula (V) in which $R'_2$ is a hydrogen atom, and the dialkylation gives compounds of formula (V) in which $R'_2$ is an alkyl, hydroxyalkyl, haloalkyl, carbalkoxyalkyl or cyanalkyl radical. In order to obtain a compound of formula (V) in which $R'_1$ and $R'_2$ represent different radicals (for example, $R'_1$=ethyl and $R'_2$=cyanethyl), it is sufficient to follow the monoalkylation by an alkylation by means of an alkylating agent different from that used for the monoalkylation.

The compounds of formula (I) in which $R_3$ represents a carbamoyl or carboxy radical may be obtained by hydrolysis of the corresponding compounds of formula (I) in which $R_3$ represents a cyano radical. However, if it is desired to prepare a compound of formula (I) where $R_3$ represents the carbamoyl or carboxy radical and $R_1$ and/or $R_2$ represents a cyanoalkyl radical, it is necessary for the hydrolysis of the cyano radical ($R_3$) to be effected before the cyanoalkylation of the compounds of formula (IV) or (V). Thus, for example, in order to prepare 3-(N-ethyl-N-cyanethylamino)hydrocinnamic acid, the monoethylation of 3-amino-hydrocinnamonitrile (formula IV with $R'_3=CN$ and $R_4=H$) is first carried out, then the hydrolysis of the 3-N-ethylamino-hydrocinnamonitrile (formula V with $R'_2=R_4=H$, $R'_3=CN$ and $R'_1=$ethyl) is effected and finally the cyanoethylation of the 3-N-ethylamino-hydrocinnamic acid thus formed.

The compounds of formula (I) in which $R_1$ and/or $R_2$ represents an alkyl radical substituted by an alkoxy or acyloxy group may be prepared from compounds of formula (I) in which $R_1$ and/or $R_2$ represents a hydroxyalkyl radical by etherification with an alcohol or by esterification with an acid chloride or anhydride.

The new compounds according to the invention are valuable intermediates for the preparation of coloring materials. They are utilizable in particular as coupling compounds for the synthesis of azo dyestuffs, especially dispersion azo dyes for polyester fibers and cationic azo dyes for acrylic fibers. The preparation of such dyestuffs is described in the concurrently filed copending applications entitled "NEW DISPERSION AZO DYESTUFFS", Ser. No. 838,327 filed Sept. 30, 1977 (Applicants: Paul M. C. Bourdauducq, Claude M. H. E. Brouard, and Jean-Pierre H. Stiot) and "NEW CATIONIC AZO DYESTUFFS", Ser. No. 838,326 filed Sept. 30, 1977 (Applicants: Claude M. H. E. Brouard, Claude L. E. Moerel, and Jean-Pierre H. Stiot), and the disclosures of said applications are incorporated herein by reference in their entireties.

The following examples, in which the parts are parts by weight unless the contrary is indicated, illustrate the invention without it being restricted thereto.

EXAMPLE 1

3-Diethylamino-hydrocinnamonitrile (or N,N-diethyl-3-β-cyanethyl-aniline)

(a) Meerwein reaction

An acid aqueous solution, freshly prepared, of the diazo compound from 138 parts of metanitraniline and a solution of 5 parts of cuprous chloride in 20 parts by volume of 19° Be hydrochloric acid were introduced, run in in parallel, into a mixture of 50 parts by volume of glacial acetic acid, 100 parts by volume of acrylonitrile and 15 parts by volume of methylethylketone. The mixture was heated to 35°–40° C. and this temperature was maintained until the diazonium salt had disappeared (about 2 hours). After cooling and filtering, 180 parts of 2-chloro-3-(3-nitro-phenyl)-propanenitrile (M.P.=90° C.) were obtained of the formula:

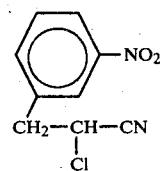

(b) Reduction

105 Parts of 2-chloro-3-(3-nitro-phenyl)-propanenitrile were introduced in small amounts, while maintaining the temperature in the vicinity of 95° C., into 500 parts of boiling water, to which had been added 100 parts of iron powder and 6 parts by volume of glacial acetic acid. The mixture was then stirred under reflux for 1 to 2 hours. At the end of the reaction, followed by chromatography on a thin layer of silica, the mixture was extracted with 100 parts by volume of chlorobenzene, then neutralized with sodium hydroxide and the iron mud was filtered off. After decantation and distillation of the chlorobenzene, 57 parts of crude 3-amino-hydrocinnamonitrile (or 3-β-cyanethyl-aniline) were obtained in the form of an oil which can be purified by subsequent distillation (B.P.=168° C./4 mm Hg).

(c) Alkylation

430 Parts by volume of diethyl sulphate were introduced drop by drop into a mixture of 146 parts of 3-β-cyanethyl-aniline, 1000 parts of water and 233 parts of sodium carbonate. The mixture was heated to 40° C. and maintained at this temperature for about 12 hours. Then 1200 parts of water were added to the reaction mixture, which was then stirred for 30 minutes, then decanted. 220 Parts of crude N,N-diethyl-3-β-cyanethyl-aniline were thus obtained of the formula:

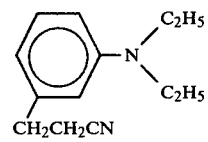

in the form of a brownish oil which can be purified by distillation (B.P.=142° C./3 mm Hg).

The retention time Tr of the N,N-diethyl-3-β-cyanethylaniline, measured at 220° C. on a Chromosorb W 15% SE 30 column of 1.5 m length and 2 mm interior diameter with an output of nitrogen of 25 ml/min., was 191 seconds.

EXAMPLE 2

Operation was as in Example 1, with the exception that the acrylonitrile was replaced by an equivalent molar amount of ethyl acrylate. N,N-diethyl-3-β-carbethoxyethyl-aniline (or ethyl-3-diethylamino-hydrocinnamate) was thus obtained, the retention time Tr of which, measured as in Example 1, was 251 seconds.

By using methyl acrylate instead of ethyl acrylate, methyl 3-diethylamino-hydrocinnamate was obtained.

EXAMPLE 3

3-N,N-bis-(β-hydroxyethyl)amino-hydrocinnamonitrile

A mixture containing 100 parts of water, 100 parts of calcium carbonate, 160 parts of glycol chlorhydrin and 73 parts of 3-amino-hydrocinnamonitrile was heated under reflux for 29 hours. It was filtered hot and washed with hot water. After decantation, 103 parts of crude 3-N,N-bis(β-hydroxyethyl)amino-hydrocinnamonitrile were obtained of the formula:

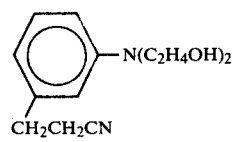

in the form of an oil which can be purified by distillation (Tr=898 s).

EXAMPLE 4

3-N,N-bis(β-acetoxyethyl)amino-hydrocinnamonitrile

A mixture of 52 parts of 3-N,N-bis(β-hydroxyethyl) amino-hydrocinnamonitrile, 100 parts by volume of glacial acetic acid and 56 parts of acetic anhydride were refluxed for 8 hours. After distillation in vacuo, 3-N,N-bis(β-acetoxyethyl)amino-hydrocinnamonitrile was obtained of the formula:

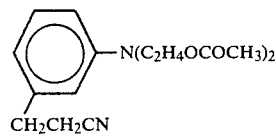

| Analysis | C% | H% | N% |
|---|---|---|---|
| Calculated for $C_{17}H_{22}N_2O_4$ | 64.1 | 6.92 | 8.80 |
| Found | 63.8 | 6.87 | 8.63 |

EXAMPLE 5

3-N-ethylamino-hydrocinnamonitrile

143 Parts by volume of diethyl sulphate were introduced drop by drop into a mixture of 146 parts of 3-amino-hydrocinnamonitrile, 1000 parts of water and 160 parts of sodium carbonate. It was heated to about 30° C. and this temperature was maintained to the end of the reaction, easily followed by chromatography on a thin layer of silica. After decantation and distillation in vacuo, 140 parts of 3-N-ethylamino-hydrocinnamonitrile were obtained which boiled at 153° C. under 2.5 mm of mercury and of which the retention time, measured as in Example 1, was 154 seconds.

EXAMPLE 6

3-(N-ethyl-N-β-cyanethyl-amino)-hydrocinnamonitrile

A mixture of 174 parts of 3-N-ethylamino-hydrocinnamonitrile, 250 parts by volume of glacial acetic acid and 64 parts of acrylonitrile was raised to 95° C. and allowed to react at 95° C. for about 24 hours. After distillation in vacuo, 3-(N-ethyl-N-β-cyanethyl-amino)-hydrocinnamonitrile was obtained of the formula:

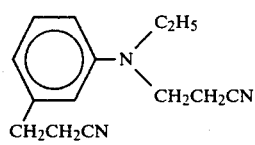

of which the rentention time, measured as in Example 1, was 552 seconds.

EXAMPLE 7

3-(N-ethyl-N-β-hydroxyethyl-amino)-hydrocinnamonitrile

A mixture of 174 parts of 3-N-ethylamino-hydrocinnamonitrile, 330 parts of glycol chlorhydrin, 200 parts of water and 200 parts of calcium carbonate was heated under reflux for about 24 hours. The product was filtered hot, washed with 60 parts of hot water, decanted and distilled in vacuo. There were thus obtained 150 parts of 3-(N-ethyl-N-β-hydroxyethyl-amino)-hydrocinnamonitrile of the formula:

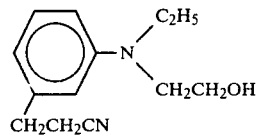

in the form of an oil which boiled at 205° C. under 2 mm of mercury.

EXAMPLE 8

3-(N-ethyl-N-β-acetoxyethylamino)-hydrocinnamonitrile

A mixture of 218 parts of 3-(N-ethyl-N-β-hydroxyethylamino)-hydrocinnamonitrile, 100 parts by volume of glacial acetic acid and 115 parts by volume of acetic anhydride was heated under reflux for 4 hours. At the end of the reaction, easily followed by chromatography on thin layers of silica, the product was neutralized with sodium carbonate and 200 parts were decanted of 3-(N-ethyl-N-β-acetoxyethyl-amino)-hydrocinnamonitrile of the formula:

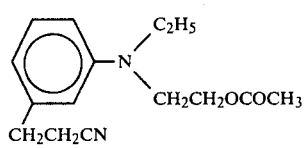

in the form of an oil which boiled at 192° C. under 20 mm of mercury.

EXAMPLE 9

The operation was as in Example 1 with the exception that the metanitraniline was replaced by 4-methyl-3-nitro-aniline. N,N-diethyl-2-methyl-5-β-cyanethyl-aniline was thus obtained of which the retention time, measured as in Example 1, was 248 seconds.

EXAMPLE 10

The operation was as in Example 1 (paragraphs a and b), with the exception that the meta-nitraniline was replaced by 4-methyl-3-nitro-aniline. The 2-methyl-5-β-cyanethyl-aniline obtained was then treated as in Example 3 by means of glycol chlorhydrin. N,N-bis(β-hydroxyethyl)-2-methyl-5-β-cyanethyl-aniline was thus obtained of which the retention time, measured as in Example 1, was 1249 seconds.

Table A below tabulates other examples of compounds of formula (I) prepared as in the preceding examples. The results of the elementary analyses of these products are according to theory.

TABLE A

| Ex. | $R_1$ | $R_2$ | $R_3$ | $R_4$ | Preparation according to the examples |
|---|---|---|---|---|---|
| 11 | $C_2H_5$ | $C_2H_5$ | CN | Cl | 1 |
| 12 | " | " | " | $OCH_3$ | 1 |
| 13 | " | " | $COOC_2H_5$ | Cl | 1 |

TABLE A-continued

| Ex. | R₁ | R₂ | R₃ | R₄ | Preparation according to the examples |
|---|---|---|---|---|---|
| 14 | " | " | " | CH₃ | 1 |
| 15 | " | " | " | OCH₃ | 1 |
| 16 | CH₂CH₂OH | CH₂CH₂OH | CN | Cl | 1a + 1b + 3 |
| 17 | " | " | " | OCH₃ | " |
| 18 | " | " | COOC₂H₅ | H | " |
| 19 | " | " | " | Cl | " |
| 20 | " | " | " | CH₃ | " |
| 21 | " | " | " | OCH₃ | " |
| 22 | CH₂CH₂OCOCH₃ | CH₂CH₂OCOCH₃ | CN | Cl | 1a + 1b + 3 + 4 |
| 23 | " | " | " | CH₃ | " |
| 24 | " | " | " | OCH₃ | " |
| 25 | " | " | COOC₂H₅ | H | " |
| 26 | " | " | " | Cl | " |
| 27 | " | " | " | CH₃ | " |
| 28 | " | " | " | OCH₃ | " |
| 29 | C₂H₅ | CH₂CH₂CN | CN | Cl | 1a + 1b + 5 + 6 |
| 30 | " | " | " | CH₃ | " |
| 31 | " | " | " | OCH₃ | " |
| 32 | " | " | COOC₂H₅ | H | " |
| 33 | " | " | " | Cl | " |
| 34 | C₂H₅ | CH₂CH₂CN | COOC₂H₅ | CH₃ | 1a + 1b + 5 + 6 |
| 35 | " | " | " | OCH₃ | " |
| 36 | " | CH₂CH₂OH | CN | Cl | 1a + 1b + 5 + 7 |
| 37 | " | " | " | CH₃ | " |
| 38 | " | " | " | OCH₃ | " |
| 39 | " | " | COOC₂H₅ | H | " |
| 40 | " | " | " | Cl | " |
| 41 | " | " | " | CH₃ | " |
| 42 | " | " | " | OCH₃ | " |
| 43 | " | CH₂CH₂OCOCH₃ | CN | Cl | 1a + 1b + 5 + 7 + 8 |
| 44 | " | " | " | CH₃ | " |
| 45 | " | " | " | OCH₃ | " |
| 46 | " | " | COOC₂H₅ | H | " |
| 47 | " | " | " | Cl | " |
| 48 | " | " | " | CH₃ | " |
| 49 | " | " | " | OCH₃ | " |
| 50 | CH₂CH₂OH | CH₂CH₂OH | COOCH₃ | H | 1a + 1b + 3 |
| 51 | CH₂CH₂OCOCH₃ | CH₂CH₂OCOCH₃ | COOCH₃ | H | 1a + 1b + 3 + 4 |
| 52 | C₂H₅ | CH₂CH₂OCOCH₃ | COOCH₃ | H | 1a + 1b + 5 + 7 + 8 |

EXAMPLE 53

3-diethylamino-hydrocinnamic acid

A mixture of 60.6 parts of 3-diethylamino-hydrocinnamonitrile, 250 parts by volume of methylated spirits of denatured alcohol, 100 parts of water and 60 parts by volume of a 35° Bé solution of sodium hydroxide was heated under reflux until the evolution of ammonia ceased. After the evolution of ammonia had stopped, the mixture was cooled and then neutralized by addition of 19° Bé hydrochloric acid. After filtering and drying, 3-diethylamino-hydrocinnamic acid was obtained of the formula:

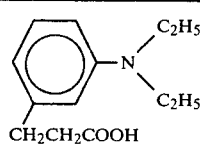

| Analysis | C% | H% | N% |
|---|---|---|---|
| Calculated for C₁₃H₁₉NO₂ | 70.5 | 8.59 | 6.34 |
| Found | 71.0 | 8.63 | 6.28 |

EXAMPLE 54

3-diethylamino-hydrocinnamamide

A mixture of 40 parts of 3-diethylamino-hydrocinnamonitrile, 34 parts by volume of 66° Bé sulphuric acid and 6 parts of water was heated at 100°–105° C. for an hour. The reaction mixture was then left to cool to about 60° C., then poured on 500 parts of ice. It was neutralized by addition of about 160 parts by volume of a 35° Bé solution of sodium hydroxide, while assuring that the temperature of the mixture did not exceed 20° C. After filtering and washing with water, 3-diethylamino-hydrocinnamamide was obtained of the formula:

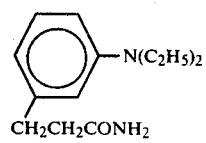

which melted at 59° C.

Table B below tabulates other examples of compounds of formula (I) where R₁=R₂=C₂H₅, prepared by operating as in Example 53 (when R₃=COOH) or as in Example 54 (when R₃=CONH₂) from the corresponding hydrocinnamonitriles (R₃=CN). The results of the elementary analyses of these products were according to theory.

TABLE B

| Example | R₃ | R₄ |
|---|---|---|
| 55 | COOH | Cl |
| 56 | COOH | CH₃ |
| 57 | COOH | OCH₃ |

TABLE B-continued

| Example | $R_3$ | $R_4$ |
|---|---|---|
| 58 | $CONH_2$ | Cl |
| 59 | $CONH_2$ | $CH_3$ |
| 60 | $CONH_2$ | $OCH_3$ |

EXAMPLE 61

3-N,N-bis(β-carbomethoxyethyl)amino-hydrocinnamonitrile

A mixture of 146 parts of 3-amino-hydrocinnamonitrile, 350 parts of glacial acetic acid, 344 parts of methyl acrylate and 1 part of hydroquinone was heated under reflux for 15 hours. It was allowed to cool to room temperature, then the mixture was poured on 3000 parts of water and neutralized to pH 7.5 by means of concentrated solution of sodium hydroxide. After decantation, 280 parts of 3-N,N-bis(β-carbomethoxyethyl)amino-hydrocinnamonitrile were obtained of the formula:

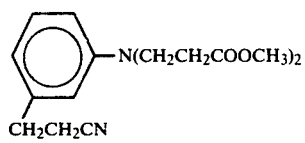

By replacing methyl acrylate with ethyl acrylate, 3-N,N-bis(β-carbomethoxyethyl)amino-hydrocinnamonitrile was obtained.

It has been found that particularly preferred N-substituted anilines of the present invention have the following formulas:

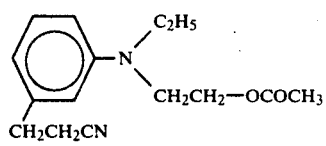

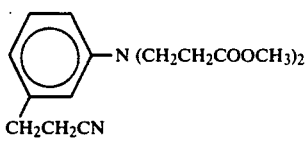

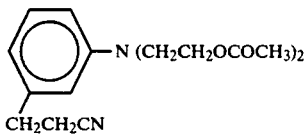

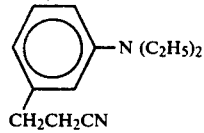

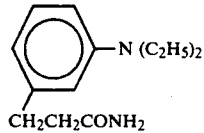

The foregoing compounds are described in Examples 8, 61, 4, 1 and 54 respectively.

What is claimed is:

1. A compound of the formula:

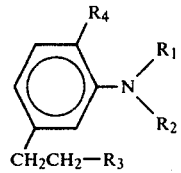

in which $R_1$ and $R_2$ each represents unsubstituted alkyl containing 1 to 4 carbon atoms or alkyl containing 1 to 4 carbon atoms monosubstituted by halogen, hydroxy, alkoxy containing 1 to 4 carbon atoms, acetoxy, propionyloxy, carbomethoxy or carbethoxy;

$R_3$ is cyano, carbamoyl, carboxy or carbalkoxy containing 2 to 5 carbon atoms; and $R_4$ is hydrogen, halogen, alkyl containing 1 to 4 carbon atoms or alkoxy containing 1 to 4 carbon atoms.

2. A compound according to claim 1 in which $R_3$ is cyano.

3. A compound according to claim 1 in which in $R_1$, $R_2$ and $R_4$ said alkyl or alkoxy contains 1 to 2 carbon atoms.

4. Compounds according to claim 1 in which $R_4$ is a hydrogen or chlorine atom or a methyl or methoxy group.

5. Compounds according to claim 1 in which each of the symbols $R_1$ and $R_2$ is ethyl, β-hydroxyethyl, β-acetoxyethyl, β-carbomethoxyethyl or β-carbethoxyethyl.

6. A compound according to claim 1 which has the formula:

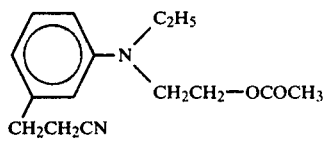

7. A compound according to claim 1 which has the formula:

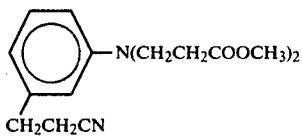

8. A compound according to claim 1 which has the formula:

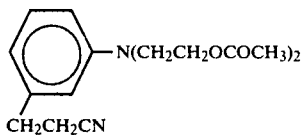

9. A compound according to claim 1 which has the formula:

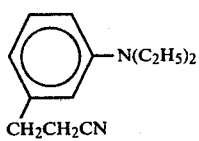
10. A compound according to claim 1 which has the formula:
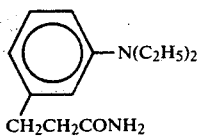
* * * * *